(12) United States Patent
Ollivier

(10) Patent No.: US 11,219,773 B2
(45) Date of Patent: Jan. 11, 2022

(54) ELECTRICAL CONNECTOR CAP FOR AN IMPLANTABLE LEAD, IMPLANTABLE LEAD FOR USE WITH SAID ELECTRICAL CONNECTOR CAP, AND IMPLANTABLE LEAD ASSEMBLY

(71) Applicant: SORIN CRM SAS, Clamart (FR)

(72) Inventor: Jean-Francois Ollivier, Gif sur Yvette (FR)

(73) Assignee: Sorin CRM SAS, Clamart (FR)

( * ) Notice: Subject to any disclaimer, the term of this patent is extended or adjusted under 35 U.S.C. 154(b) by 408 days.

(21) Appl. No.: 16/135,949

(22) Filed: Sep. 19, 2018

(65) Prior Publication Data
US 2019/0083795 A1 Mar. 21, 2019

(30) Foreign Application Priority Data

Sep. 20, 2017 (EP) .................................... 17306231

(51) Int. Cl.
*A61N 1/05* (2006.01)
*A61N 1/375* (2006.01)
(Continued)

(52) U.S. Cl.
CPC ......... *A61N 1/3752* (2013.01); *A61N 1/0529* (2013.01); *A61N 1/0551* (2013.01);
(Continued)

(58) Field of Classification Search
CPC ................................ A61N 1/05; A61N 1/3752
See application file for complete search history.

(56) References Cited

U.S. PATENT DOCUMENTS 8,000,808 B2 * 8/2011 Hegland ................ A61B 5/287
607/122
8,600,518 B2 * 12/2013 Meadows ................ A61N 1/05
607/116
(Continued)

FOREIGN PATENT DOCUMENTS

CN 106232181 A 12/2016
EP 1 641 084 B1 3/2006
(Continued)

OTHER PUBLICATIONS

Second Office Action on Chinese application No. 201811087335.6 dated Jun. 23, 2020. 10 pages.
(Continued)

*Primary Examiner* — George R Evanisko
(74) *Attorney, Agent, or Firm* — Foley & Lardner LLP

(57) ABSTRACT

The present disclosure relates to an electrical connector cap, in particular for an implantable lead, the electrical connector cap comprising an elongated body having at least one lumen and at least one through hole extending from an outer surface of the elongated body into the lumen, and at least one electrically conductive member arranged on an outer circumference of the elongated body over said at least one through hole of the elongated body. Furthermore, said at least one electrically conductive member comprises at least one through hole (extending from an outer surface of the electrically conductive member into the lumen through said at least one through hole of the elongated body. The disclosure further relates to implantable lead assemblies comprising said electrical connector cap, and to an implantable lead member usable with said electrical connector cap.

16 Claims, 10 Drawing Sheets

(51) Int. Cl.
   *A61N 1/362* (2006.01)
   *A61N 1/36* (2006.01)
   *A61N 1/39* (2006.01)

(52) U.S. Cl.
   CPC .......... *A61N 1/0563* (2013.01); *A61N 1/3601* (2013.01); *A61N 1/362* (2013.01); *A61N 1/3605* (2013.01); *A61N 1/37512* (2017.08); *A61N 1/3968* (2013.01)

(56) References Cited

U.S. PATENT DOCUMENTS

| | | |
|---|---|---|
| 2003/0195602 A1 | 10/2003 | Boling |
| 2004/0068303 A1 | 4/2004 | Ostroff |
| 2011/0245887 A1* | 10/2011 | Klardie .................. A61N 1/05 607/2 |
| 2012/0089203 A1 | 4/2012 | Shaffer |

FOREIGN PATENT DOCUMENTS

| | | |
|---|---|---|
| EP | 2 559 453 A1 | 2/2013 |
| EP | 2 647 406 A1 | 10/2013 |
| EP | 2 664 354 A1 | 11/2013 |
| WO | WO-98/48887 A1 | 11/1998 |
| WO | WO-2014/101200 A1 | 7/2014 |

OTHER PUBLICATIONS

Search Report on European Patent Application No. 17306231.6 dated May 9, 2018. 10 pages.
First Chinese Office Action on Application No. 201811087335.6 dated Oct. 9, 2019. 19 pages.

* cited by examiner

ELECTRICAL CONNECTOR CAP FOR AN IMPLANTABLE LEAD, IMPLANTABLE LEAD FOR USE WITH SAID ELECTRICAL CONNECTOR CAP, AND IMPLANTABLE LEAD ASSEMBLY

CROSS-REFERENCE TO RELATED PATENT APPLICATIONS

This application claims the benefit of and priority to European Application No. 17306231.6, filed Sep. 20, 2017, which is incorporated herein by reference in its entirety.

BACKGROUND

The present disclosure relates to the field of active medical implantable devices, such as implantable pacemakers and/or defibrillators. The present disclosure relates, in particular, to an electrical connector cap, to an implantable lead assembly, and to an implantable lead or lead member for use with said electrical connector cap.

As illustrated schematically in FIG. 1, a known implantable lead 1 for an active implantable medical device such as an implantable pacemaker and/or defibrillator typically comprises an elongated lead body 2, a proximal end 3 configured to be plugged in a dedicated socket of the housing of the active implantable medical device, and a distal end 4 configured for sensing and/or stimulating a tissue. For illustrative purposes, the lead body 2 is interrupted rather than being illustrated in its full length, and only portions towards both ends thereof are represented.

The proximal end 3 of a known implantable lead 1 typically comprises a pluggable electrical connector portion 5, which is usually configured according to standards of the art. For instance, the pluggable electrical connector portion 5 can be configured as a standard IS-1 or DF-1 connector, as explained in EP 1 641 084 B 1, or following more recent developments, as a standard IS-4 or DF-4 connector. In the latter standards, as schematically illustrated on FIG. 1, the connector portion 5 comprises a series of three electrically conductive rings 6, 7, 8 spaced apart from one another in the longitudinal direction of the connector portion 5, and an axial contact pin 9 protruding from the free end of the connector portion 5. Typically, the rings 6, 7, 8 and pin 9 are dedicated to low voltage lines in leads destined for simulation, such as leads using a standard IS-4 connector. In contrast, in leads destined also for defibrillation, such as leads using a standard DF-4 connector, two electrically conductive rings 6, 7 are dedicated to high voltage lines, while the third electrically conductive ring 8 and the axial contact pin 9 are dedicated to low voltage lines.

Furthermore, in the particular case of standard IS-4 and DF-4 connectors, the diameter and length of the connector portion 5 and the spacing and size of the rings 6, 7, 8 are essentially the same. Therefore, in order to avoid the unintentional insertion of a lead of a given type in the wrong socket of the housing of the active implantable medical device, the sockets of the housing and, accordingly, the axial contact pin 9 of the connector portion 5 are shaped differently for each standard type.

In turn, the distal end 4 of a known implantable lead 1 typically comprises a series of electrodes 10, 11, 12 connected to a respective one of the rings 6, 7, 8 of the pluggable electrical connector portion 5 via a respective electrically conductive line 13, 14, 15 arranged in the lead body 2, which is usually tubular and comprises at least one main lumen (not illustrated in FIG. 1 for the sake of simplicity), in which one or more of the electrically conducting lines 13, 14, 15 is arranged. Depending on the type of lead 1, the lead body 2 can also be of the multi-lumen type, in which case each electrically conductive line 13, 14, 15 can be arranged in a respective (secondary) lumen extending parallel to a main lumen. Furthermore, another electrically conductive line (also not illustrated for the sake of simplicity) can also be linked to the axial pin 9 and be arranged, in particular, also in the main lumen.

As also schematically illustrated in FIG. 1, in particular in dotted area 16, the lead body 2 and the connector portion 5 are manufactured as separate components. In particular, the lead body 2 and the connector portion 5 are manufactured with respective portions of electrically conductive wires 13a, 14a, 15a and 13b, 14b, 15b that need to be connected to one another in order to form the electrically conductive lines 13, 14, 15. In a classic approach, this is achieved by gluing and welding the ends of portions 13a, 14a, 15a to the respective ends of portions 13b, 14b, 15b, and then forming an insulation between and around the exposed part of the thereby formed electrically conductive lines 13, 14, 15 so as to essentially complete and extend the lead body 2 up to the interface with the connector portion 5.

A drawback of the classic approach is that known implantable leads, such as the lead 1 schematically described with reference to FIG. 1, present various weaknesses in the area where the lead body joins the connector portion. In other words, in the area where the two portions of each electrically conductive line 13, 14, 15 are joined or interconnected, which is regularly submitted to intensive mechanical stress, both in tension and flexion, ranging from the doctor's manipulation during the implantation procedure to everyday movements of a patient with an implanted device, that can damage the electrically conductive lines, especially at the interconnections.

This problem is both relevant for stimulation leads, using for instance the IS-4 standard, which have very thin electrically conductive wires, and for defibrillation leads, using for instance the DF-4 standard, which use micro-cables that are known to be resistant in tension but not so much in flexion (typically, micro-cables can be flexible elements having a diameter of at most 2 French or 0,66 mm, as described, for instance, in EP 2 559 453 A1 and EP 2 664 354 A1). Thus, in both types of leads, an excessive mechanical stress applied at the junction between the electrical connector and the lead body could result in a break of one or more of the interconnections due to mechanical fatigue.

Thus, a technical problem relates to ensuring reliable interconnections of the portions of electrically conductive wires 13a, 14a, 15a and 13b, 14b, 15b forming each electrically conductive line 13, 14, 15. Another technical problem relates to ensuring a reliable electrical insulation between the different electrically conductive lines 13, 14, 15, especially between the high voltage lines (represented schematically by electrically conductive lines 13, 14 in FIG. 1).

SUMMARY

In view of the above, an object of the present disclosure is to limit the number of interconnections in the electrically conductive lines and, if possible, even to avoid having interconnections in the electrically conductive lines in the lead body. At the very least, it is desirable to move any necessary interconnection in the electrically conductive lines to areas of an implantable lead being less subject to mechanical stress than the junction between the lead body and the connector in order to avoid a possible break of one or more electrically conductive line due to mechanical fatigue.

Furthermore, in the classic approach, series of connector portions, such as the connector portion 5 schematically described reference to FIG. 1, are manufactured in lines of production specifically dedicated to a predefined standard of connectivity. For instance, a given line of production outputs only IS-4 standard connectors or only DF-4 standard connectors.

Thus, an object of the present disclosure is also to standardize even more the connector portion of an implantable lead while also overcoming the above-mentioned technical problems.

According to an aspect of the present disclosure, the above-mentioned objects are achieved with an electrical connector cap according to claim 1. The electrical connector cap comprises an elongated body having at least one lumen and at least one through hole extending from an outer surface of the elongated body into the lumen, and at least one electrically conductive member arranged on an outer circumference of the elongated body over said at least one through hole of the elongated body. Furthermore, said at least one electrically conductive member comprises at least one through hole extending from an outer surface of the electrically conductive member into the lumen through said at least one through hole of the elongated body.

The present disclosure thereby provides an electrical connector cap that can be mounted, in particular, over a terminal end portion of the body of an implantable lead to be received in the lumen of the electrical connector cap. It is, therefore, possible to extend the lead body so that its proximal or terminal end can be accommodated within the lumen of the electrical connector, rather than being joined to a connector portion as explained above with reference to FIG. 1. As a consequence, the interconnections between said at least one electrically conductive member of the electrical connector cap and any corresponding electrically conductive wire(s) in the lead body can be realized within the electrical connector cap, in particular by means of the through hole of the electrically conductive member reaching into the lumen of the electrical connector cap, and which can facilitate the welding process, in particular a laser welding. In other words, the present disclosure completely avoids having these interconnections in the area of the lead body immediately following the electrical connector cap, which is the area of the implantable leads known to be submitted to intensive mechanical stress.

Furthermore, by providing an electrical connector cap rather than an entire connector portion like in the classical approach described above with reference to FIG. 1, it is possible to completely standardize the electrical connector cap as a separate component which can be used for any type of standard. For instance, since the dimensions of standard IS-4 and DF-4 connectors are essentially the same, the present disclosure provides an electrical connector cap that can be used for both standards while being manufactured in a single production line. The difference between two standards having overall similar dimensions, such as the IS-4 and DF-4 standards, then only needs to be made at the level of the axial contact pin, which is provided at the proximal end of the lead body to be received in the electrical connector cap according to the present disclosure, and when needed at the level of the preferred type of lead body used for this standard (single main lumen, multi-lumen, etc.).

Here, it is to be understood that the electrical connector cap of the present disclosure is a separate component destined to form an electrical connector plug when mounted onto the proximal end of an implantable lead, which is intended to be plugged into a mating socket of the housing of an active medical implantable device such as an implantable pacemaker and/or defibrillator.

Furthermore, in the present disclosure, it is to be understood that a "through hole" is distinct from a "lumen", a "lumen" being here understood essentially as being a bore in the longitudinal direction of the lead body, which can be commonly an elongated structure, essentially in a tubular shape, and a "through hole" being here understood as being an opening through the side wall of the lead body extending between the outer surface thereof and a lumen of the lead body. In addition, the terms "proximal" or "proximal end" of a device or structure will be used to refer to the direction or end intended to be facing the socket of the housing of an active medical implantable device, and the term "distal" or "distal end" will be used to refer to the opposite direction or end (for instance, the end of an implantable lead comprising the sensing/stimulating electrodes).

In addition, although implantable leads for cardiac applications are mentioned, the present disclosure is not limited thereto. Essentially any type of implantable lead could benefit from using the electrical connector cap of the present disclosure, which can have as many electrically conductive members as required by the application. Thus, in cardiac applications using the IS-4 or DF-4 connectivity standards, a connector cap according to the present disclosure could comprise three electrically conductive members corresponding to three electrical lines, the fourth electrical line being connected to the axial pin of the lead. However, the disclosure could be adapted to pulmonary applications or even to neurology. For instance, a connector according to the present disclosure could be used with an implantable lead for stimulation of brain areas or stimulations of the spinal cord, wherein a plurality of electrical lines, for instance up to 16 electrical lines (or more if necessary) are used.

Further advantageous aspects and variants are also described in the dependent claims and will become more evident in the following disclosure.

According to an embodiment, when the elongated body has more than one through hole, one or more through holes can be offset longitudinally along the elongated body with respect to each other. According to another embodiment, when the elongated body has more than one through hole, one or more through holes can be offset in a circumferential direction of the elongated body with respect to each other, in particular evenly along the circumferential direction. These alternative or complementary configurations are advantageous as they provide different entry points that facilitate establishing electrical connections for implantable leads comprising a plurality of electrically conductive lines.

According to an embodiment, the elongated body can be a one-piece component. In a variant of an embodiment, the elongated body can be made of an insulating material, in particular a biocompatible insulating material. Thus, the electrical connector cap of the present disclosure can be manufactured by simple techniques, for instance by molding the elongated body in one piece, and then over-molding one or more electrically conductive members on the elongated body.

According to an embodiment, the elongated body can have an essentially cylindrical shape, and the lumen can be about the longitudinal axis of the elongated body. This configuration is advantageous, as it can be adapted to known standards of implantable leads and associated connector plugs.

According to an embodiment, the diameter of the lumen can be constant over a main central portion of the elongated body and can decrease at a proximal end portion of the elongated body. According to a variant of an embodiment, the diameter of the lumen can decrease stepwise at the proximal end portion. Thus, the lumen of the electrical connector cap of the present disclosure can be advantageously sized not only for receiving therein a lead body of a predetermined diameter, but also for receiving a lead body already comprising an axial connecting pin at its proximal end.

According to an embodiment, the diameter of the lumen can be larger at a distal end portion of the elongated body than at a main central portion of the elongated body. The electrical connector cap can thereby advantageously receive therein a lead body comprising for instance one or more additional protective and/or insulating sleeve(s).

According to an embodiment, a distal end portion of the elongated body can comprise at least one additional through hole, in particular free of any electrically conductive member. This configuration advantageously provides mechanical support for attaching a member to the electrical connector cap. For instance it can provide mechanical support for attaching a protective and/or insulating sleeve covering at least partially the distal end portion of the electrical connector cap and/or a part of a lead body emerging from the electrical connector cap.

According to an embodiment, an outer diameter of the elongated body can decrease, in particular stepwise, at a distal end portion thereof. This configuration is advantageous in order to facilitate the attachment of a protective and/or insulating sleeve over a distal end portion of the electrical connector cap and at least the part of the lead body emerging from the electrical connector cap in and assembled implantable lead.

According to an embodiment, the elongated body can comprise at least one recessed area along an outer circumference, said at least one through hole being in a corresponding recessed area, and said at least one electrically conductive member being arranged in a respective recessed area. This configuration facilitates the over-molding and positioning of one or more electrically conductive members. Advantageously, the positioning of said recessed area(s) can be chosen so as to match a predefined standard (IS-4, DF-4, or the like).

According to a variant of an embodiment, said at least one recessed area can extend along a complete outer circumference of the elongated body, in particular said at least one recessed area can be essentially annular. This configuration allows advantageously providing one or more ring-shaped electrically conductive members, the dimensions of which can also be adapted so as to match a predefined standard (IS-4, DF-4, or the like).

According to an embodiment, an outer surface of said at least one electrically conductive member can be flush with the outer surface of the elongated body. This configuration is advantageous as it allows providing an electrical connector cap pluggable into standardized sockets (IS-4, DF-4, or the like).

According to an embodiment, said at least one electrically conductive member can have an inner protrusion extending in the respective through hole of the elongated body, in particular extending radially inwards. According to a variant of an embodiment, said inner protrusion can be flush with the inner surface or lumen of the elongated body. These alternative or complementary configurations are advantageous as they facilitate establishing the interconnection between an electrically conductive member of the electrical connector cap and a respective electrically conductive line having, for instance, an electrical contact emerging at the level of the inner protrusion. Operations like laser welding are thereby facilitated.

According to a further variant of an embodiment, said at least one through hole of said at least one electrically conductive member can extend through said inner protrusion, in particular radially. This configuration is advantageous as it facilitates even more establishing the interconnections, especially when laser welding techniques are used.

According to another aspect of the present disclosure, the above-mentioned object is also achieved with an implantable lead assembly according to claim 14. The implantable lead assembly comprises an elongated lead body having a proximal end, being the end of the lead body destined to be connected to a housing of an active implantable medical device, and a distal end, being the opposite end of the lead body configured for sensing and/or stimulating a tissue, and at least one lumen, and at least one electrically conductive wire arranged in said at least one lumen, said at least one electrically conductive wire being in electrical contact, at the distal and proximal ends, with a respective distal or proximal electrically conductive member provided on an outer circumference of the lead body. Furthermore, the implantable lead assembly comprises, mounted over the proximal end, an electrical connector cap according to the previous aspect of the present disclosure, such that a proximal electrically conductive member at least partially contacts a respective electrically conductive member of the electrical connector cap.

Here, it is understood that a lead body can have only one main lumen or a plurality of lumina, and that a given lumen may be centered of off-centered with respect to a main axis of the elongated lead body. In embodiments for which the lead body can be a multi-lumen lead body, it could comprise a main lumen and the at least one lumen can be one or more secondary lumen, different from the main lumen. For instance, one or more lumen can be arranged essentially parallel to the main lumen. In this case, it is understood that the "main" lumen does not need to be a "central" lumen and can, itself, be off-centered with respect to a main axis of the elongated lead body. In any case, with the present disclosure, it is possible to improve implantable lead assemblies using different types of elongated bodies, single lumen or multi-lumen.

According to an embodiment, said at least one electrically conductive wire can be a micro-cable. When applied to implantable leads used also for defibrillation purposes, for instance of the DF-4 type, the present disclosure advantageously provides protection against bending stress for micro-cables, which are otherwise known to be resistant in tension but not in bending. The present disclosure can, otherwise, also be used for other standards, for instance the IS-4 standard, for which other types of electrically conductive wires are used.

According to an embodiment, said implantable lead assembly can further comprise an axial pin protruding from the proximal end of the lead body and from the proximal end of the electrical connector cap. The axial pin can be arranged rotatably with respect to the lead body and/or to the electrical connector cap. Thus, it is possible to provide, when necessary, a fourth electrical line connected to the axial pin and/or an optional internal coil with a fastening mechanism, such as a screw, can be provided within the implantable lead.

According to an embodiment, said at least one proximal electrically conductive member can be an emerging junction and/or an at least partially ring-shaped element. Depending on the preferred configuration, it is therefore possible to provide implantable leads destined for different uses, for instance defibrillation and/or cardiac pacing. Indeed, the type of proximal electrically conductive member(s) can be adapted to the type of lead body used. For instance, without being restricted thereto, proximal electrically conductive members realized as emerging junctions could be preferred for multi-lumen lead bodies, and substantially ring-shaped proximal electrically conductive members could be preferred for single-lumen lead bodies. In some embodiments, combinations of both emerging electrical junctions and ring-shaped members could be used.

According to another aspect of the present disclosure, the above-mentioned object is also achieved with an implantable lead member according to claim 16, in particular by an implantable lead member destined to be used with an electrical connector cap according to one of the previous aspects of the present disclosure or any variant thereof. The implantable lead member comprises an elongated lead body having a proximal end, being the end of the lead body destined to be connected to a housing of an active implantable medical device, and a distal end, being the opposite end of the lead body configured for sensing and/or stimulating a tissue, and at least one lumen. The lead member further comprises at least one electrically conductive wire arranged in said at least one lumen, said at least one electrically conductive wire being in electrical contact, at the distal and proximal ends of the lead body, with a respective distal or proximal electrically conductive member provided on an outer circumference of the lead body. In the lead member, at least one proximal electrically conductive member is at least partially ring-shaped.

Thus, an aspect of the disclosure can provide an implantable lead member suitable for use with an electrical connector cap according to previous aspects of the disclosure or any variant thereof.

According to an embodiment, said at least one proximal electrically conductive member can be an open ring-shaped element. It can, therefore, be slid over the lead body along its main axis, or clipped onto the lead body, or even clipped and then slid along the longitudinal direction of the elongated lead body.

Furthermore, a circumference of said at least one proximal electrically conductive member can extend over more than about 180°. This has the advantage that guiding, in particular radial guiding, of an electrical connector cap according to the previous aspects of the disclosure or any of their variants is facilitated when the electrical connector cap is fitted over the proximal end of the implantable lead member according to this aspect.

According to an embodiment, an internal diameter of said at least one proximal electrically conductive member can correspond substantially to an external diameter of said elongated lead body. This has the advantage that the proximal electrically conductive member can be securely assembled, in particular, clipped, to the lead body.

According to an embodiment, said at least one proximal electrically conductive member can comprise a groove or a notch. It is thereby possible to provide an electrical contact area for an electrically conductive wire, in particular for an emerging electrically conductive wire. This is advantageous to protect the underlying lead body when the electrically conductive wire needs to be fixedly secured to the ring-shaped proximal electrically conductive member. For instance, when laser welding technology is used to this purpose, the groove or notch accommodating the electrically conductive wire can protect the underlying lead body from being damaged by the laser welding process.

According to another aspect of the present disclosure, as set forth in claim 20, the above-mentioned object is also achieved with an implantable lead assembly combining the implantable lead member and the electrical connector cap of the previous aspects and any variants thereof. The implantable lead assembly, therefore, comprises an implantable lead member according to a previous aspect or any variant thereof, and, mounted over the proximal end thereof, an electrical connector cap according to a previous aspect or any variant thereof, wherein an outer diameter of said at least one proximal electrically conductive member corresponds substantially to an inner diameter of the lumen of the electrical connector cap, whereby said at least one proximal electrically conductive member at least partially contacts a respective electrically conductive member of the electrical connector cap.

Accordingly, the lead member can, therefore, also be standardized, and it can also be used for different types of leads, depending on the final desired configuration of the optional axial contact pin as explained above.

Thus, an aspect of the present disclosure has the advantage that a lead member according to a previous aspect of the disclosure can be used in combination with an electrical connector cap of another previous aspect, or any variants thereof, in order to form variants of an implantable lead assembly.

An implantable lead as described above, namely provided with an electrical connector cap according to the previous aspect of the disclosure, and an implantable lead member destined to be used with said electrical connector cap, also present all the advantages described above.

BRIEF DESCRIPTION OF THE DRAWINGS

Additional features and advantages will be described hereafter with reference to the accompanying figures, wherein.

DETAILED DESCRIPTION

It is understood that the accompanying figures and the following description are intended to illustrate preferred embodiments of the disclosure, and that these embodiments do not necessarily represent the full scope of the disclosure.

In the following description, the same reference signs may be used to designate the same features throughout the figures illustrating a particular embodiment. Furthermore, without being restricted thereto, similar reference signs may be used to designate the same or similar features in different embodiments.

Embodiments of an electrical connector cap 20 will first be described with reference to FIGS. 2A and 2B. Although the electrical connector cap 20 will be described mainly in reference to the IS-4 and DF-4 standards, it is understood that the present disclosure is not limited thereto, and that the shape, dimensions, and arrangements described hereafter could be adapted to other connectivity standards for implantable leads of other types. For instance, the present disclosure could be used also for brain and/or spinal stimulation leads, which typically comprise more electrically conductive lines than in current cardiac applications.

Figure 2A:
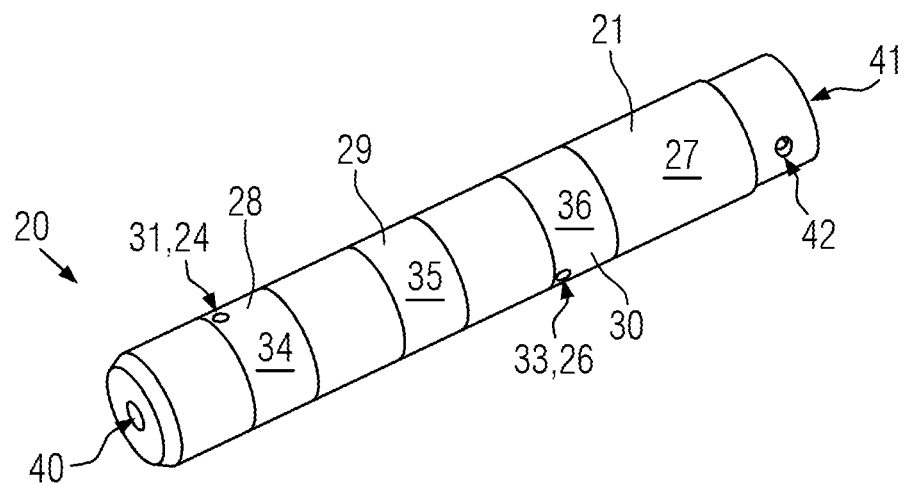
FIGS. 2A and 2B illustrate embodiments of an electrical connector cap.
Figure 2B:
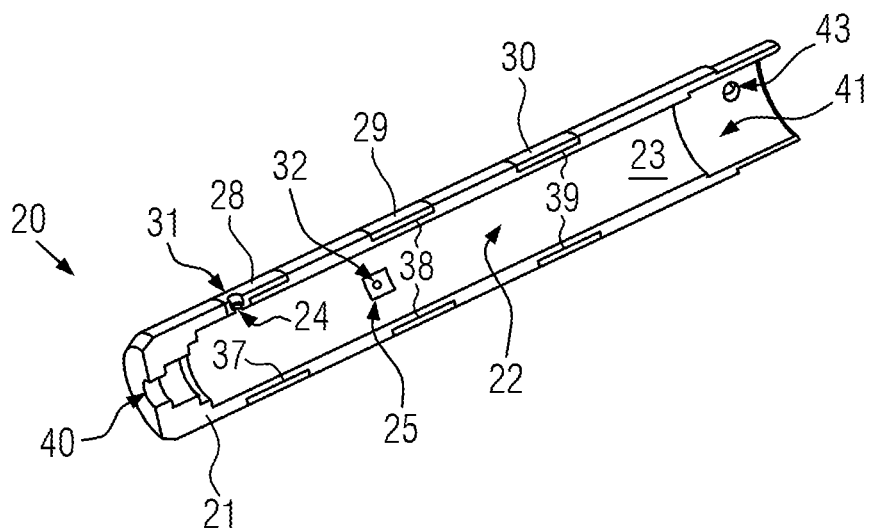

In any case, the inventive electrical connector cap 20 comprises an elongated body 21 with at least one lumen 22 defining an inner surface 23 of the elongated body 21, as can be seen in the sectional view of FIG. 2B. According to one embodiment, the elongated body 21 can be essentially tubular, as illustrated in FIGS. 2A and 2B, without however being restricted only to a tubular shape, and the lumen 22 can be centered on the main axis of the elongated body 21. The illustrate shape is preferred as it corresponds to standards of the art regarding connector plugs of implantable leads. However, the present disclosure may also be applied to other standards requiring a different shape for the elongated body.

Furthermore, according to an embodiment, the elongated body 21 can be a one-piece component, which is preferred as it facilitates its production, for instance, using known molding techniques. In addition, the elongated body 21 can preferably be made of a biocompatible insulating material. Without being limited thereto, the elongated body 21 can be made of thermoplastic polyurethane, which can be preferably transparent or semi-transparent for better visual control of the welding and/or gluing with a lead body received in the lumen 22. A transparent or semi-transparent elongated body 21 could generally be advantageous for visual inspection of any alignment, welding, gluing, or any other process that needs to be carried out inside the electrical connector cap 20.

Furthermore, the elongated body 21 comprises at least one through hole extending between the outer surface 27 of the elongated body 21 and the lumen 22. It is understood that the number of through holes can vary depending, in particular, on how many electrically conductive lines and how many contact points for these lines need to be established in an implantable lead on which the electrical connector cap 20 is to be mounted. In the embodiment illustrated in FIGS. 2A and 2B, the elongated body 21 comprises three through holes 24, 25, 26. Although some of the visible through holes, here though holes 24, 25 on FIG. 2B, are illustrated with an essentially square shape, it is understood that this specific shape is not limitative for the scope of the present disclosure. In other words, the elongated body of an electrical connector cap may comprise one or more through holes of any desired shape.

Furthermore, according to an embodiment, one or more through holes 24, 25, 26 can be essentially along a radial direction of the elongated body 21. However, in other embodiments, one or more through holes don't need to be exactly along a radial direction and could have a slope. In addition, according to embodiments of the present disclosure illustrated in FIGS. 2A and 2B, the through holes 24, 25, 26 can be offset with respect to each other in the longitudinal and/or in a circumferential direction of the elongated body 21, which can facilitate the interconnection with more than one electrically conductive line, as will be become more evident with the embodiments illustrated in FIGS. 4A and 4B.

Following an aspect of the disclosure, the electrical connector cap 20 comprises at least one electrically conductive member arranged on a circumference of the outer surface 27 of the elongated body 21, an electrically conductive member comprising at least one through hole extending from its outer surface into the lumen 22 via a respective through hole of the elongated body 21. In the embodiment illustrated on FIGS. 2A and 2B, the electrical connector cap 20 comprises three electrically conductive members 28, 29, 30, which are essentially electrical contact ports, having each a through hole 31, 32, 33 extending from the outer surface 34, 35, 36 of the respective electrically conductive member 28, 29, 30 into the lumen 22 via a respective through hole 24, 25, 26 of the elongated body 21. An example of an electrically conductive member 50 will be discussed more in detail hereafter with reference to FIG. 3.

Furthermore, in the embodiments illustrated in FIGS. 2A and 2B, the elongated body 21 comprises, along respective circumferences at the level of the through holes 24, 25, 26, recessed areas 37, 38, 39, which can facilitate over-molding of the electrically conductive members 28, 29, 30. In particular, the position, number, and dimensions of the electrically conductive members 28, 29, 30 can be adapted to standards such as the IS-4 and DF-4 standards. In other embodiments, the position, number, and dimensions of electrically conductive members could be adapted to other connectivity standards or requirements.

According to an embodiment, also illustrated in FIGS. 2A and 2B, the lumen 22 can have an essentially constant diameter over almost the entire length of the elongated body 21, and can decrease at the proximal end, which is the end intended to face the mating socket of the housing of an active implantable medical device, whereby the opening 40 of the elongated body 21 at the proximal end can be sized to the dimensions, in particular, the diameter, of an axial contact pin at the terminal end of a lead body to be received within the electrical connector cap 20. The decreasing diameter of the lumen 22 at the proximal end of the electrical connector cap 20 can be achieved in one or more steps or continuously, this aspect not being limitative for the scope of the present disclosure.

Regarding the distal end of the electrical connector cap 20, which is the end intended to receive a lead body, according to other embodiments, also illustrated in FIGS. 2A and 2B but not intended to be limited to for the scope of the present disclosure, the diameter of the lumen 22 can be slightly larger than in the main section. This can facilitate reception of a lead body comprising, for instance, additional protective and/or insulating sleeve(s) in the distal opening 41 of the electrical connector cap 20. Furthermore, the outer diameter of the elongated body 21 could optionally also be reduced at the distal end, in particular, in one or more steps or continuously, which may also facilitate reception of additional protective and/or insulating sleeve(s) for better protection and/or insulation of at least the part of a lead body and emerging from the distal end of the electrical connector cap 20 mounted thereon.

According to yet another embodiment, the distal end of the electrical connector cap 20, in particular, the distal end of the elongated body 21, can be provided with one or more additional through holes, different from through holes 24, 25, 26 in that they are preferably free of any electrically conductive member. In the embodiment illustrated in FIGS. 2A and 2B, two through holes 42, 43 are visible at the distal end of the elongated body 21. These additional through holes 42, 43 can be used for facilitating the mechanical attachment of an additional protective and/or insulating sleeve which could be used to protect and/or insulate the area where a lead body would emerge from the distal end of the electrical connector cap 20.

An example of an electrically conductive member 50 of an electrical connector cap according to embodiments of the present disclosure will now be described with reference to FIG. 3. For the sake of simplicity, the electrically conductive member 50 corresponds essentially to any one of the electrically conductive members 28, 29, 30 of the embodiments described with reference to FIGS. 2A and 2B. This example is, however, not intended to be limitative for the scope of the present disclosure. For instance, when the electrical connector cap has more than one electrically conductive member, the shape and dimensions of the electrically conductive members do not need to be the same.

In the embodiments illustrated in FIGS. 2A and 2B, the elongated body 21 has ring-shaped recessed areas 37, 38, 39. A suitable electrically conductive member 50 can, therefore, also be essentially ring-shaped, as illustrated in FIG. 3. Furthermore, according to an embodiment, the outer surface 51 of the electrically conductive member 50 can be flush with the outer surface of the elongated body of the electrical connector cap. This can also be seen in FIGS. 2A and 2B, wherein the outer surfaces 34, 35, 36 of the electrically conductive members 28, 29, 30 are represented flush with the outer surface 27 of the elongated body 21. These configurations, although not intended to be limitative for the scope of the present disclosure, are advantageous because they allow an electrical connector cap to be adapted to standards of the art, such as the IS-4 and DF-4 standards, or analog standards. However, the electrically conductive member(s) of the electrical connector cap does not need to be ring-shaped or flush with the outer surface of the elongated body. In other embodiments still falling within the scope of the present disclosure, an electrically conductive member could, for instance, be an open ring, in other words an arc of a ring, or adopt any another shape suitable to a different shape of the elongated body.

Figure 3:
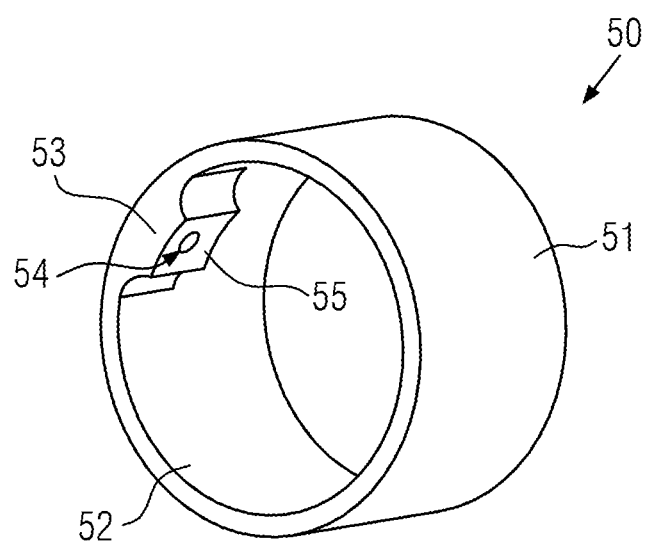
FIG. 3 illustrates an exemplary electrically conductive member of embodiments of an electrical connector cap.

As can be taken from FIG. 3, according to another embodiment, the electrically conductive member 50 can be provided with an inner protrusion 53 extending inwardly from the inner surface 52 of the electrically conductive member 50. As can be taken from the disclosure above, the electrically conductive member 50 of the embodiments illustrated in FIG. 3 could be over-molded directly on an elongated body, in particular, in a recessed area thereof, whereby the inner protrusion 53 would be directly molded in a corresponding through hole of the elongated body and would have the corresponding dimensions. Following another embodiment, the inner protrusion 53 could be made flush with the inner surface or lumen of the elongated body of the electrical connector cap. In particular, the free end or surface 55 of inner protrusion 53 could be made flush with the inner surface or lumen of the elongated body. As also illustrated in FIG. 3, the inner protrusion 53 can be provided so as to include the through hole 54 of the electrically conductive member 50, which can be particularly advantageous in order to establish interconnections using laser welding techniques.

Most of these optional features can also be seen to some extent in FIG. 2B for electrically conductive member 28, which is illustrated with a similar inner protrusion extending in through hole 24. In other words, in the embodiments illustrated in FIGS. 2A and 2B, the electrically conductive member 28, 29, 31 could be provided, at the location of the respective through holes 24, 25, 26, with inner protrusions similar to inner protrusion 53 of electrically conductive member 50 extending in a respective through hole 24, 25, 26 of the elongated body 21. Furthermore, the respective free end of these inner protrusions could be flush with the inner surface 23 of the elongated body 21 as defined by lumen 22.

The previous aspects and embodiments, as well as advantages of different aspects of the disclosure, will be explained hereafter with reference to FIGS. 4A and 4B, which schematically illustrate the assembly of embodiments of an electrical connector cap 60 with a lead member 70, forming embodiments of an implantable lead assembly 100 according to another aspect of the present disclosure. In particular, FIG. 4A illustrates the electrical connector cap 60 next to the lead member 70 and not assembled, and FIG. 4B illustrates the assembled implantable lead assembly 100 with the electrical connector cap 60 mounted onto the lead member 70.

Here, the electrical connector cap 60 comprises an elongated body 61 having therein a lumen 62 extending between a proximal opening 66 and a distal opening 67, and on which three electrically conductive members 63, 64, 65 are provided, in particular, longitudinally spaced apart from one another. As mentioned above, the choice of three electrically conductive members may be particularly advantageous when taken in conjunction with the IS-4 and DF-4 standards. However, as also mentioned above, the present disclosure can be adapted to other connectivity standards or requirements, such that embodiments of the electrical connector cap may comprise more or less than three electrically conductive members without diverging from the scope of the present disclosure.

Figure 4A:
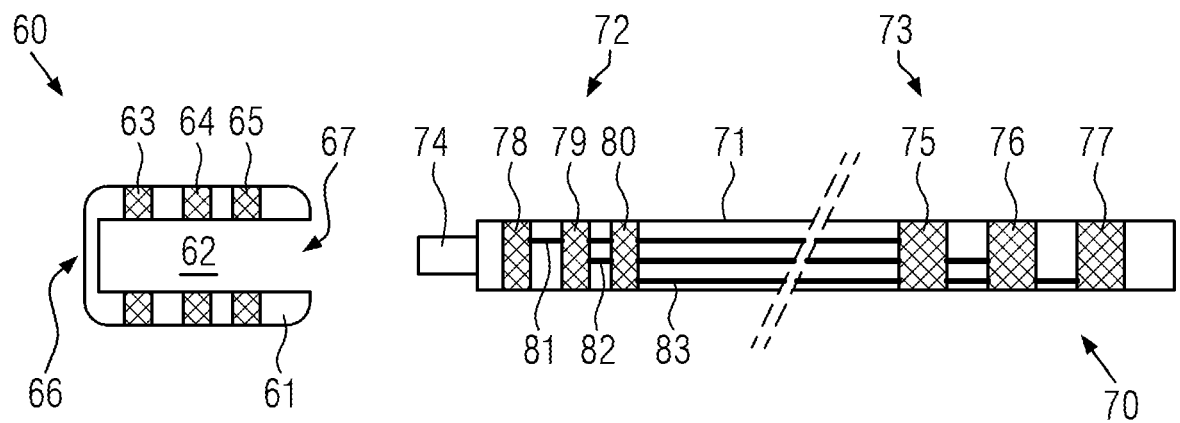
FIGS. 4A and 4B schematically illustrate the assembly of embodiments of an electrical connector cap with a lead body, forming embodiments of an implantable lead assembly.
Figure 4B:
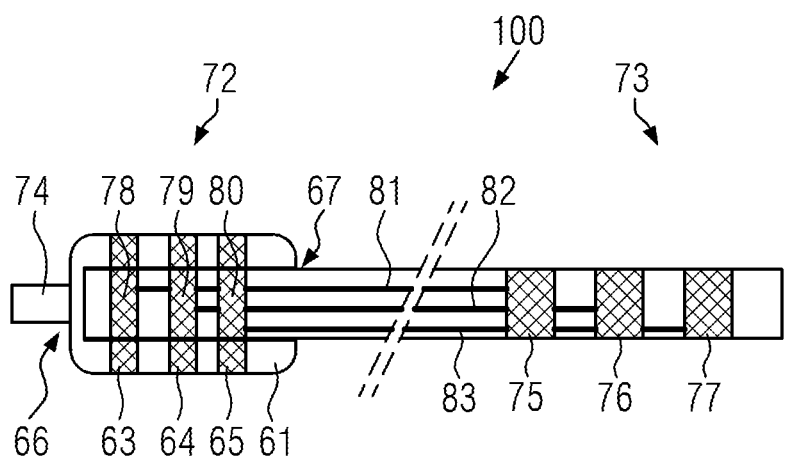

Although illustrated in a simplified manner, the embodiments represented in FIGS. 4A and 4B will be used to discuss aspects and advantages mentioned above. Thus, it is understood that, for the sake of comprehension, the electrical connector cap 60 represented in FIGS. 4A and 4B can correspond to any embodiment or combination of embodiments described above, or variants thereof. In particular, the electrical connector cap 60 could be the electrical connector cap 20 or variants thereof, and the electrically conductive members 63, 64, 65 could be the electrically conductive members 28, 29, 30 or the electrically conductive member 50, or variants thereof, described above. The skilled reader is, therefore, referred back to the disclosure above. In particular, while the embodiments discussed hereafter present particular advantages for standardizing even more the components used in the context of IS-4 and DF-4 connections, the skilled person in the field of implantable leads will be able to recognize that the teachings of the present disclosure can be adapted to other standards.

As can be taken from FIGS. 4A and 4B, the lead member 70 usable with the electrical connector cap 60 to form an implantable lead assembly 100 according to an aspect of the disclosure has an elongated lead body 71, which can be essentially in a tubular shape, having a proximal end 72 and a distal and 73. For illustrative purposes, the lead body 71 is interrupted rather than being illustrated in its full length, and only portions towards both ends thereof are represented. Furthermore, the lead body 71 comprises at least one lumen, which is not illustrated for the sake of simplicity. Depending on embodiments, the lead body 71 can have only one main lumen, or it can be a multi-lumen lead body 71. The proximal end 72 is configured to be received in the electrical connector cap 60 and, when assembled therewith, be plugged in a dedicated socket of the housing of an active implantable medical device. In turn, the distal end 73 is configured for sensing and/or stimulating a tissue.

Figure 1:
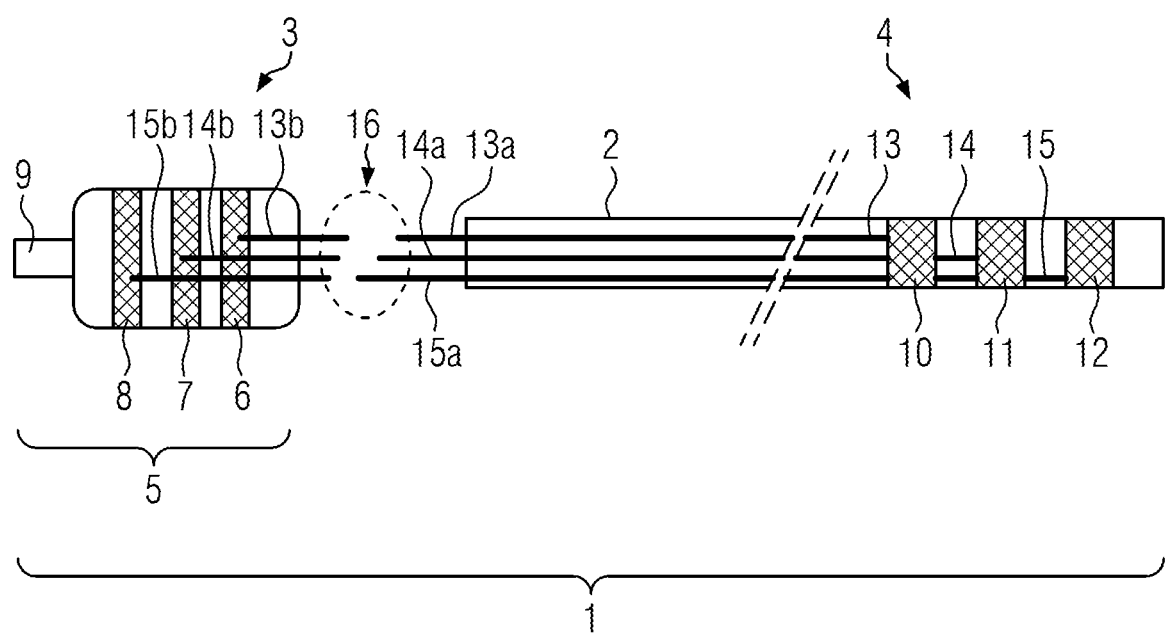
FIG. 1 schematically illustrates a known implantable lead, detailing in particular a known connection between the lead body and the end portion of the implantable lead comprising the connector plug, which will be useful to understand the present disclosure.

Similar to the implantable lead 1 illustrated in FIG. 1, the distal end 73 of lead member 70 can comprise a series of distal electrode, here represented as ring-shaped electrodes 75, 76, 77. However, in contrast with the classic approach illustrated in FIG. 1, each distal electrode 75, 76, 77 of the lead member 70 of the embodiments illustrated in FIGS. 4A and 4B is connected to a respective proximal contact port, here represented as ring-shaped contact ports 78, 79, 80, which are electrically conductive members that can be similar to the distal electrodes 75, 76, 77 in most aspects. In particular, the contact ports 78, 79, 80 could be realized using the same techniques as for the distal electrodes 75, 76, 77, which can facilitate the overall manufacturing process of the lead member 70. However, it is understood that the proximal contact ports could be realized in a different manner according to, for instance as junctions emerging from the lead body 71, and/or even as closed or open rings, as will be detailed hereafter in the embodiments described with reference to FIGS. 5 to 10.

Furthermore, one or more electrically conductive wires, here at least the three visible electrically conductive wires 81, 82, 83, are arranged within the lead body 71. Depending on the type of lead body 71, all or only some of the electrically conductive wires, for instance electrically conductive wires 81, 82, 83, may be arranged within a single main lumen, or each one within a respective lumen of a multi-lumen lead body. In any case, also in contrast with the classic approach, no interconnection is necessary in the electrically conductive lines realized by the electrically conductive wires 81, 82, 83 connecting the distal electrodes 75, 76, 77 to the proximal contact ports 78, 79, 80. The skilled person will appreciate this technical advantage over the classic approach, advantage which can be adapted to other numbers of electrically conductive lines, distal electrodes, and proximal contact ports in other embodiments when other standards than IS-4 or DF-4 are used.

As can be taken from the disclosure above, in order to be compatible for both the IS-4 and the DF-4 standards, the electrical connector cap 60 does not include an axial pin. Thus, an axial pin 74 can be mounted at the proximal end 72 of the lead member 70, as illustrated schematically in FIG. 4A. Accordingly, it is also possible to dedicate one or more electrically conductive member(s) of the electrical connector cap 60, here for instance electrically conductive members 64, 65, to high voltage lines. It is also possible to dedicate one or more electrically conductive member(s), here for instance electrically conductive members 63, and/or the axial pin 74 to low voltage lines. In some embodiments, the axial pin 74 can be rotatable with respect to the lead member 70, in particular with respect to the lead body 71. Without being limited thereto, at least in some embodiments for which the implantable lead assembly 100 is a defibrillation lead, the axial pin 74 can be rotatable with respect to the electrical connector cap 60.

In an assembled state of the implantable lead assembly 100, as illustrated in FIG. 4B, the electrical connector cap 60 is fully mounted over the proximal end 72 of the lead member 70. In other words, the proximal end 72 of the lead member 70 is fully inserted in the electrical connector cap 60, with the proximal end 72 in abutment against the proximal opening 76 of the electrical connector cap 60 and the axial pin 74 and having been inserted and protruding through said proximal opening 76.

The interconnections between the electrically conductive members 63, 64, 65 of the electrical connector cap 60 and the proximal contact ports 78, 79, 80 of the proximal end 72 of the lead member 70 can then be realized by known techniques, in particular by laser welding. This operation is facilitated by the presence of a through hole in the electrically conductive members 63, 64, 65 as described in the previous embodiments. Depending on the shape of the proximal electrically conductive members provided on a lead body used with an electrically connector cap according to the present disclosure, which may be different from the ring-shaped contact ports 78, 79, 80, it may be necessary to align the through holes of the electrically conductive members 63, 64, 65 with an underlying contact port or proximal electrically conductive member of the lead body. This could be necessary, for instance, if these elements are realized as junctions emerging from the lead body instead of the ring-shaped contact ports 78, 79, 80 of the embodiment illustrated in FIGS. 4A and 4B. When the electrically conductive members 63, 64, 65 comprise an inner protrusion like in the embodiments described with reference to FIG. 3, a physical connection may be achieved between the electrically conductive members 63, 64, 65 and the contact ports 78, 79, 80, especially when the latter emerge from the lead body 70, such that a high-quality interconnection may be achieved, especially when laser welding techniques are used.

Furthermore, after welding and/or gluing, as applicable, one or more protective and/or insulating sleeve (not illustrated) may be added over the distal end of the electrical connector cap 60 and at least a portion of the lead body 70 emerging from the distal opening 67. Advantageously, when the distal end portion of the elongated body 61 of the electrical connector cap 60 comprises one or more additional through holes like the additional through holes 42, 43 described in previous embodiments with reference to FIGS. 2A and 2B, it is possible to use these additional through holes 42, 43 as mechanical attachment points for said protective and/or insulating sleeve.

When the electrical connector cap 60 is mounted and fixed to the proximal end 72, in particular by laser welding and/or gluing as described above, the distinction between the IS-4 and DF-4 type can be made, for instance, by adapting the part of the axial pin 74 protruding from the proximal opening 66 of the electrical connector cap 60 to an axial pin pluggable in the socket of the desired connector type. This can be achieved by welding an IS-4 or DF-4 profiled contact pin (not illustrated) onto the protruding axial pin 74, thereby realizing an implantable lead assembly 100 whose connector plug is according to the desired standard. In other embodiments, other profiled contact pins may be welded onto the axial pin protruding from the proximal opening of the electrical connector cap assembled to a lead member in order to achieve a connector plug according to any other desired standard.

The skilled person will appreciate that other distinctions may also be made at the level of the type of lead member 70 (single main lumen, multi-lumen, etc.) and electrically conductive wires (or micro-cables when applicable) used to realize the electrically conductive lines, as well as their particular arrangement within the lead member 70, and the type of proximal contact ports emerging from the lead member 70.

Examples of implantable lead members and implantable lead assemblies according to aspects of the present disclosure will be described hereafter with reference to FIGS. 5 to 10. In particular, examples of an implantable lead member 200 and corresponding implantable lead assembly 210 will be described in conjunction with FIGS. 5 to 7, and examples of an implantable lead member 300 and corresponding implantable lead assembly 310 will be described with reference to FIGS. 8 to 10. In particular, the implantable lead members 200, 300 illustrated in FIGS. 5 to 7 and in FIGS. 8 to 10, respectively, will be used as examples of how to adapt a lead body of the multi-lumen type or of the type comprising only one main lumen, respectively, for use with an electrical connector cap according to the disclosure above to thereby form a corresponding implantable lead assembly also according to the present disclosure.

Furthermore, in the following embodiments, the implantable lead members 200, 300 will be used, respectively, with an electrical connector cap according to aspects already described above, to thereby form implantable lead assemblies 210, 310, as explained for instance with reference to FIGS. 4A and 4B. Thus, in the following embodiments, an electrical connector cap can also be one of the electrical connector caps 20, 60 already described above, or any variant thereof. For details regarding particular aspects of an electrical connector cap according to the disclosure, the reader is referred back to the description above, in particular to the embodiments described with reference to FIGS. 1 to 3. For further details regarding implantable lead assemblies according to the disclosure, the reader is also referred back to the description above, in particular to the embodiments described with reference to FIGS. 4A and 4B.

In any case, like in the previous embodiments, the description of the embodiments illustrated with reference to FIGS. 5 to 10 will focus on the respective proximal end of a lead member 200, 300, which is the end thereof configured to be connected to the housing of an active implantable medical device. The description of the distal end of a lead member 200, 300, which is the end thereof configured for sensing and/or stimulating a tissue, will however be omitted, as it can be realized according to well-known techniques as also explained above.

Figure 5:
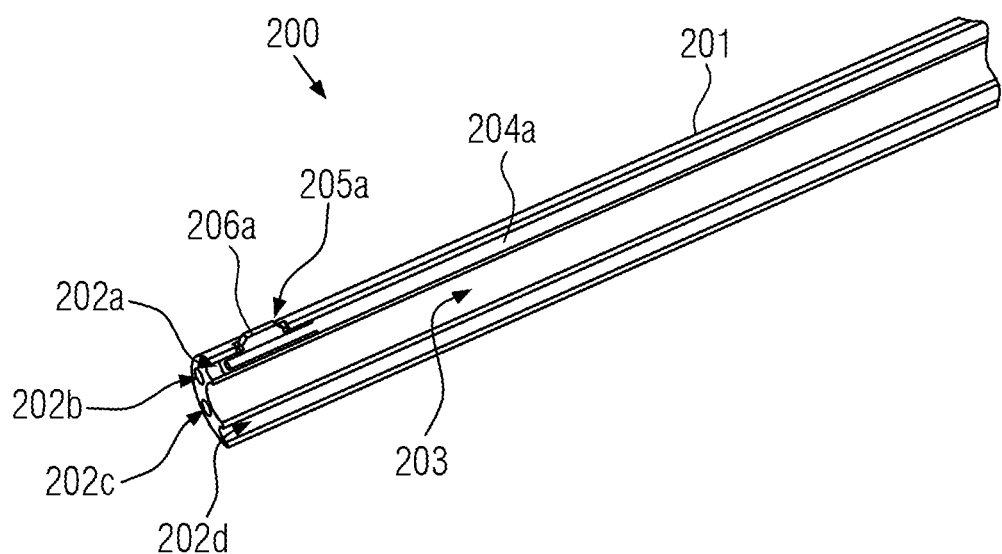
FIG. 5 schematically illustrates a longitudinal sectional view of the proximal end of a lead body usable with embodiments of an electrical connector cap.
Figure 6:
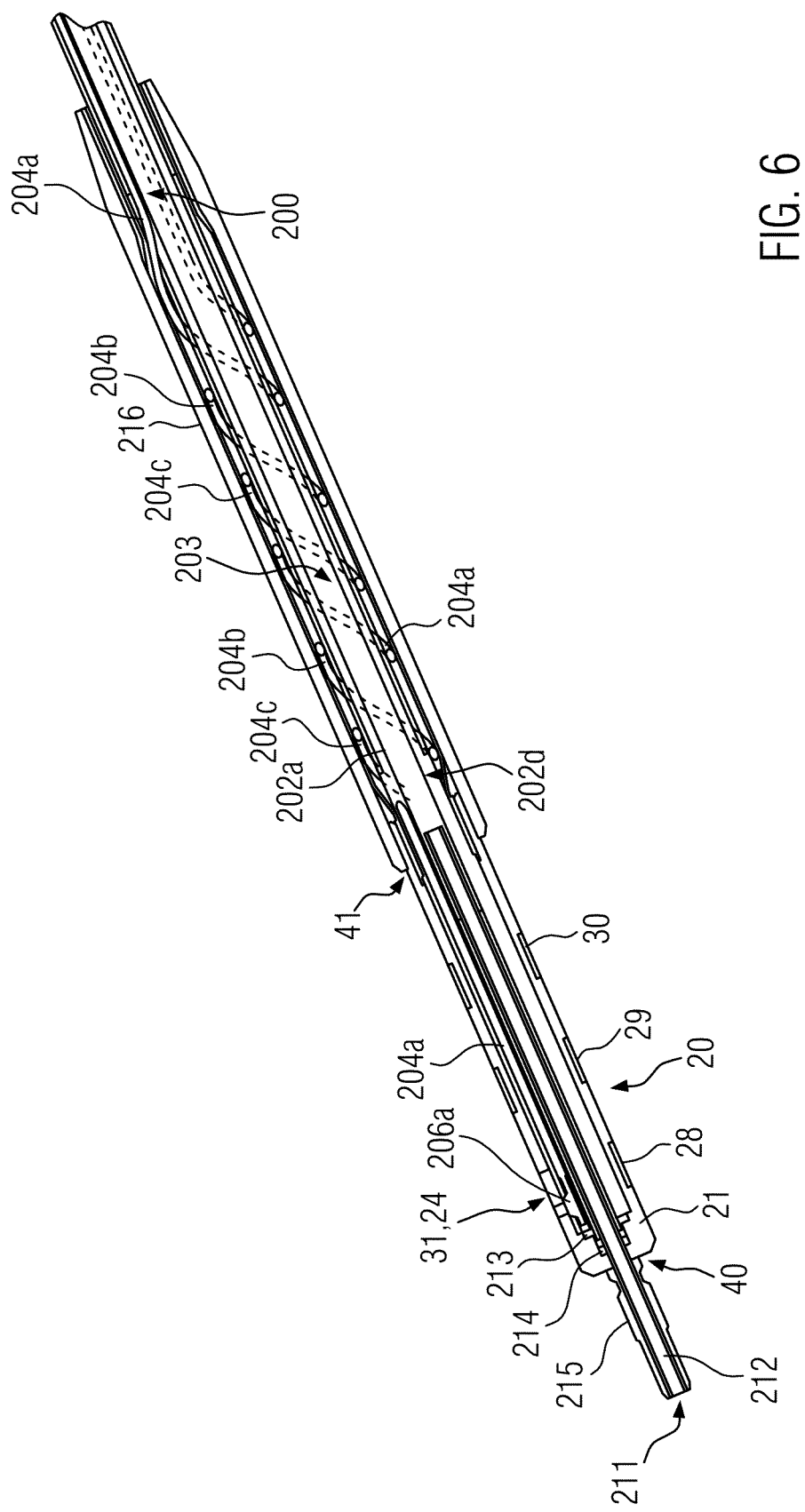
FIG. 6 schematically illustrates a longitudinal sectional view of embodiments of an implantable lead assembly, comprising the electrical connector cap of the embodiments illustrated in FIGS. 2A and 2B mounted over the proximal end of a lead body according to the example illustrated in FIG. 5.
Figure 7:
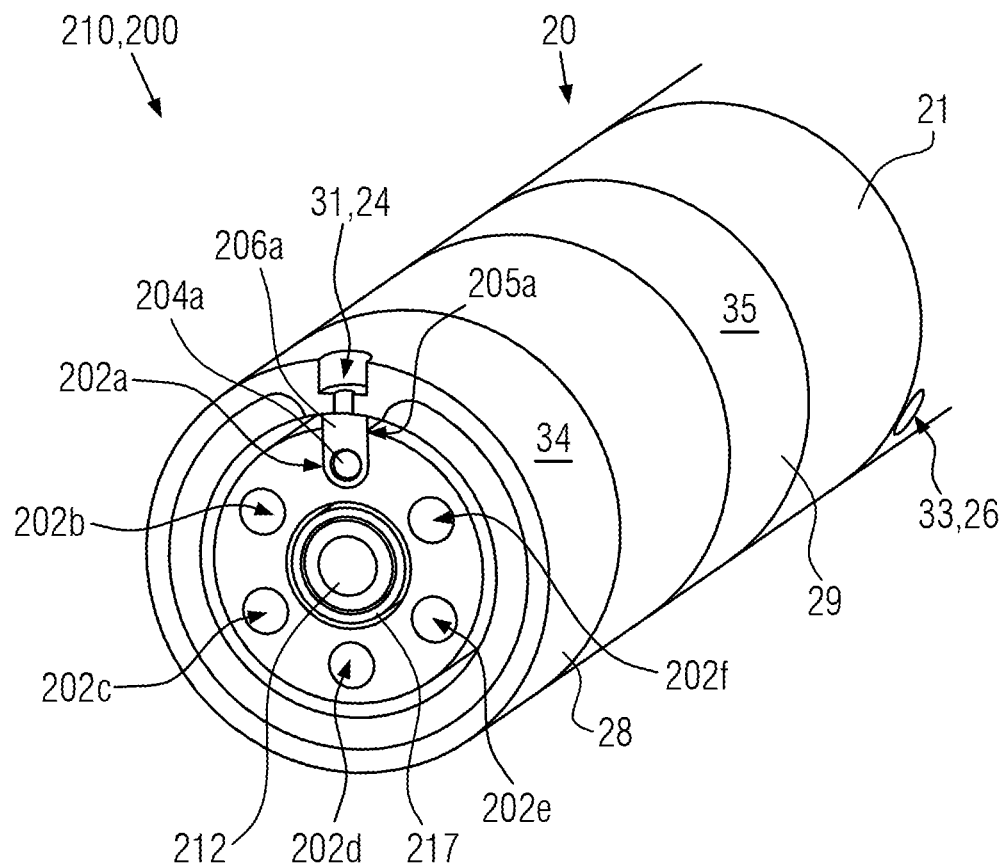
FIG. 7 schematically illustrates a cross-sectional view of the implantable lead assembly illustrated in FIG. 6 detailing a contact area between respective electrically conductive members of the lead and of the electrical connector cap.

The embodiments illustrated in FIGS. 5 to 7 will be used, in particular, to describe the proximal end of an implantable lead of the defibrillation type, for instance an implantable lead configured according to the DF-4 standard, and to illustrate an example of how to achieve proximal electrically conductive members in a multi-lumen lead body. It is understood that the particular connectivity standard is merely used for the sake of this example and is not intended to be limitative for the scope of the present disclosure.

As can be taken from the longitudinal sectional view of FIG. 5, an implantable lead member 200 usable with an electrical connector cap according to the previous aspects of the present disclosure can comprise an elongated body 201, which is here essentially tubular and of the multi-lumen type, having a main lumen 203 surrounded by a plurality of secondary lumina 202a, 202b, 202c, 202d, 202e, 202f, the last two being only visible in the cross-sectional view of FIG. 7. Without being restricted thereto, the lead body 201 can therefore be made by extruding or molding a biocompatible, preferably flexible, material such as polyurethane. It is to be understood that the relative arrangement and diameter of the various lumina 202a, 202b, 202c, 202d, 202e, 202f and 203 is not limitative for the present disclosure, and that other relative arrangements and configurations of a multi-lumen body could also be adapted to achieve the same functionality, in particular be made compatible for use with an electrical connector cap according to aspects of the present disclosure.

Furthermore, one or more of the secondary lumina 202a, 202b, 202c, 202d, 202e, 202f can accommodate therein a respective electrically conductive wire to form electrically conductive lines between proximal and distal electrically conductive members. For instance, as explained above, in the DF-4 standard, three electrically conductive lines could be realized in three respective lumina out of lumina 202a, 202b, 202c, 202d, 202e, 202f, and one (or more) electrically conductive line could also be realized in the main lumen 203. For the sake of simplicity, only one electrically conductive line is represented by means of electrically conductive wire 204a in lumen 202a, but more electrically conductive wires 204b, 204c can be identified in the implantable lead assembly 210 illustrated in FIG. 6. As mentioned above, an electrically conductive wire could be realized as a micro-cable, which is preferred in particular for leads intended for defibrillation purposes, hence for an implantable lead of the DF-4 type.

In addition, as can be seen in FIGS. 5 to 7, proximal electrically conductive members of a lead member usable in combination with an electrical connector cap, like the proximal electrically conductive members 78, 79, 80 of the embodiments illustrated in FIGS. 4A and 4B, can be achieved as emerging junctions. Here, this is achieved by means of a respective terminal end or electrical contact 206a provided at the proximal end of electrically conductive wire 204a, which emerges out of lumen 202a via a respective through hole 205a at the proximal end of the lead body 201. In some embodiments, the electrical contact 206a can be attached, for instance by welding and/or crimping and/or gluing and/or any other known method, to the end of electrically conductive wire 204a. Since more than electrically conductive line can be provided, as many such electrical contacts may be provided as emerging junctions towards the proximal end of any other lumen accommodating therein an electrically conductive wire. In other words, the configuration illustrated with wire 204a, through hole 205a and contact 206a could be replicated for any other lumen 202b, 202c, 202d, 202e, 202f (or optionally even lumen 203) having accommodated therein an electrically conductive wire like wire 204a in lumen 202a, hence here also for wires 204b, 204c. In the present embodiments, three emerging junctions in the form of, and including, emerging electrical contacts like contact 206a can be provided in three lumina, including lumen 202a, when the lead member 200 is destined to be a defibrillation lead of the DF-4 standard type, each one being destined to contact a respective electrically conductive member of an electrical connector cap according to the present disclosure. To facilitate operations, when several emerging junctions are provided, they can be spaced apart on the circumference and/or longitudinal direction of the lead body 201. Preferably the longitudinal separation between successive emerging junctions can correspond to the separation between successive electrically conductive members 28, 29, 30 or 78, 79, 80 of an electrical connector cap 20 or 60 according to the present disclosure.

Thus, in contrast with known implantable leads discussed above, it is possible to provide an implantable lead member 200 in which no interconnections (within the meaning discussed above) are realized to form electrically conductive lines between the distal electrodes and the proximal end of the lead body. This is possible since the emerging electrical contacts correspond essentially to terminal ends of the various electrically conductive wires as illustrated for the lead member 200, wherein electrical contact 206*a* corresponds essentially to a terminal end for electrically conductive wire 204*a*.

FIG. 6 illustrates a longitudinal sectional view of an implantable lead assembly 210 according to aspects of the disclosure, formed by the implantable lead member 200 illustrated in FIG. 5 onto which the electrical connector cap 20 (or 60) of the embodiments illustrated in FIGS. 2A and 2B (or 4A and 4B) is mounted. FIG. 7 illustrates a cross-sectional view of the implantable lead assembly 210. Accordingly, an electrical connector cap according to the disclosure is mounted on the proximal end of the lead member 200 illustrated in FIG. 5. This forms an implantable lead assembly 210 similar to the lead assembly 100 described in the embodiments with reference to FIGS. 4A and 4B. For the sake of simplicity, the electrical connector cap 20 illustrated in FIGS. 6 and 7 is the same as in FIGS. 2A and 2B. It is understood that it can also be the electrical connector cap 60 of the embodiments illustrated in FIGS. 4A and 4B, or any variant described above. The reader is, therefore, also referred back to the disclosure above.

Optionally, before mounting the electrical connector cap 20 on the proximal end of the lead member 200, a contact pin assembly 211 can have been mounted in the main lumen 203 of the lead body 201. As can be taken from FIG. 6, the contact pin assembly 211 can comprise an axial contact pin 212, partly accommodated in the main lumen 203 of the lead body 201, and partly protruding from the proximal end of the lead body 201. If so desired, the part of the axial contact pin 212 accommodated in the main lumen 203 can be covered by an optional insulating sleeve 217, visible at least in FIG. 7, preferably of biocompatible material, and the contact pin assembly 211 can also comprise further elements such as a one or more optional stop rings 213, and one or more optional seal rings 214, along the axial contact pin 212. In some embodiments, an optional internal coil with a fastening mechanism, such as a screw (not illustrated), can be provided within the implantable lead assembly 210, in particular through the main lumen 203 and/or the axial contact pin 212, which can then be preferably tubular. Preferably, the axial contact pin 212 can be provided so as to be rotatable relative to the lead body 201. Furthermore, the axial contact pin 212 can also be connected to a distal sensing and/or stimulating electrode via an electrically conductive wire. Furthermore, the part of the axial contact pin 212 of the contact pin assembly 211 protruding through the proximal end of the body 21 of the electrical connector cap 20 can be configured according to a specific connectivity standard. To this purpose, a terminal end 215 configured, in particular shaped, for the desired specific standard can be provided over the protruding part of the axial contact pin 212, as illustrated in FIG. 6. To this purpose, the terminal end 215 could, for instance, be attached using known welding, laser welding, or other known methods. In the illustrated embodiments, terminal end 215 can be configured, in particular shaped, to correspond to the DF-4 standard. Although this example is intended to illustrate a particular type of standard connector, it is understood that other embodiments could relate to different types of standard connectors without diverging from the scope of the present disclosure.

Furthermore, as illustrated in FIGS. 6 and 7, when the electrical connector cap 20 is mounted over the proximal end portion of the lead member 200, because its electrically conductive members 28, 29, 30 extend into lumen 22 via respective through holes 24, 25, 26 of the elongated body 21 of the electrical connector cap 20, it is possible to arrange the part of an electrically conductive member 28, 29, 30 extending in a respective through hole 24, 25, 26 of the electrical connector cap 20 so as to face a respective emerging electrical contact of a respective electrically conductive line of the lead member 200. In the embodiments illustrated in FIGS. 6 and 7, the electrically conductive members 28, 29, 30 are realized like the ring-shaped electrically conductive member 50 of the embodiments illustrated in FIG. 3. When the electrical connector cap 20 is mounted on the proximal end of the lead member 200, the respective inner protrusion of an electrically conductive member 28, 29, 30 can consequently establish a physical contact with an underlying respective electrical contact emerging from the lead member 200. Here, as illustrated in FIG. 6 and especially in FIG. 7, the inner protrusion of electrically conductive member 28 faces and contacts electrical contact 206*a*. The through hole 31 of the electrically conductive member 28 can facilitate visual control of the position of the underlying emerging electrical contact 206*a* relative to the electrically conductive member 28, hence control of the mounted position of the electrical connector cap 20 on the proximal end of the lead body 201. It can also facilitate using techniques such as laser welding in order to fixedly secure the electrically conductive member 28 to the emerging electrical contact 206*a*. This operation can, of course, be repeated for as many electrically conductive members 28, 29, 30 and underlying respective emerging electrical contacts as necessary in order to fixedly secure the electrical connector cap 20 to the lead member 210. It is optionally also possible to further attach and insulate the electrical connector cap 20 to the lead member 200, in particular to the lead body 201, for instance by injecting an adhesive through one or more other through holes provided in the lead body 201 and/or between the lead body 201 and the elongated body 21 of the electrical connector cap 20, so as to fill any spaces or volumes therebetween.

In the embodiments illustrated in FIGS. 5 to 7, it is therefore possible to achieve an implantable lead assembly 210 that can be used, in particular, for cardiac defibrillation when combined with a housing comprising DF-4 type sockets. In this case, the electrical lines using electrically conductive members 29, 30 could be high voltage lines, and the electrical lines using electrically conductive member 28 and the contact pin assembly 211 could be low voltage lines. The particular connectivity standard and the assignment of low and/or high voltage lines are, however, not limitative for the scope of this disclosure.

In addition, as illustrated in FIG. 6, an implantable lead assembly 210 can comprise one or more protective and/or reinforcing and/or insulating sleeves like sleeve 216, which can be slid over the lead body 201 and, preferably, also over a rear or distal portion of the electrical connector cap 20 and be attached thereto, in particular using an adhesive and/or mechanical means. For instance, sleeve 216 could be clipped to the rear part or distal portion of electrical connector cap 20 using the additional through holes 42, 43. In this way, it is possible to reinforce, protect and/or insulate the portion of the lead body 201 emerging from the electrical connector cap 20. For instance, it is possible to prevent body fluids from penetrating, in particular filtering, into the distal portion of the electrical connector cap 20, thereby increasing the prevention against electrical shortages. The optional sleeve 216 can be made of silicon or any other suitable flexible biocompatible material.

In the following, the embodiments illustrated in FIGS. 8 to 10 will be used, in particular, to describe the proximal end of an implantable lead of the stimulation or pacing type, for instance an implantable lead configured according to the IS-4 standard, and to illustrate an example of how to achieve proximal electrically conductive members in a lead body comprising only one lumen. Again, it is understood that the particular connectivity standard is merely used to illustrate an application of the disclosure but should not be viewed as being limitative for the scope of the present disclosure.

Figure 8:
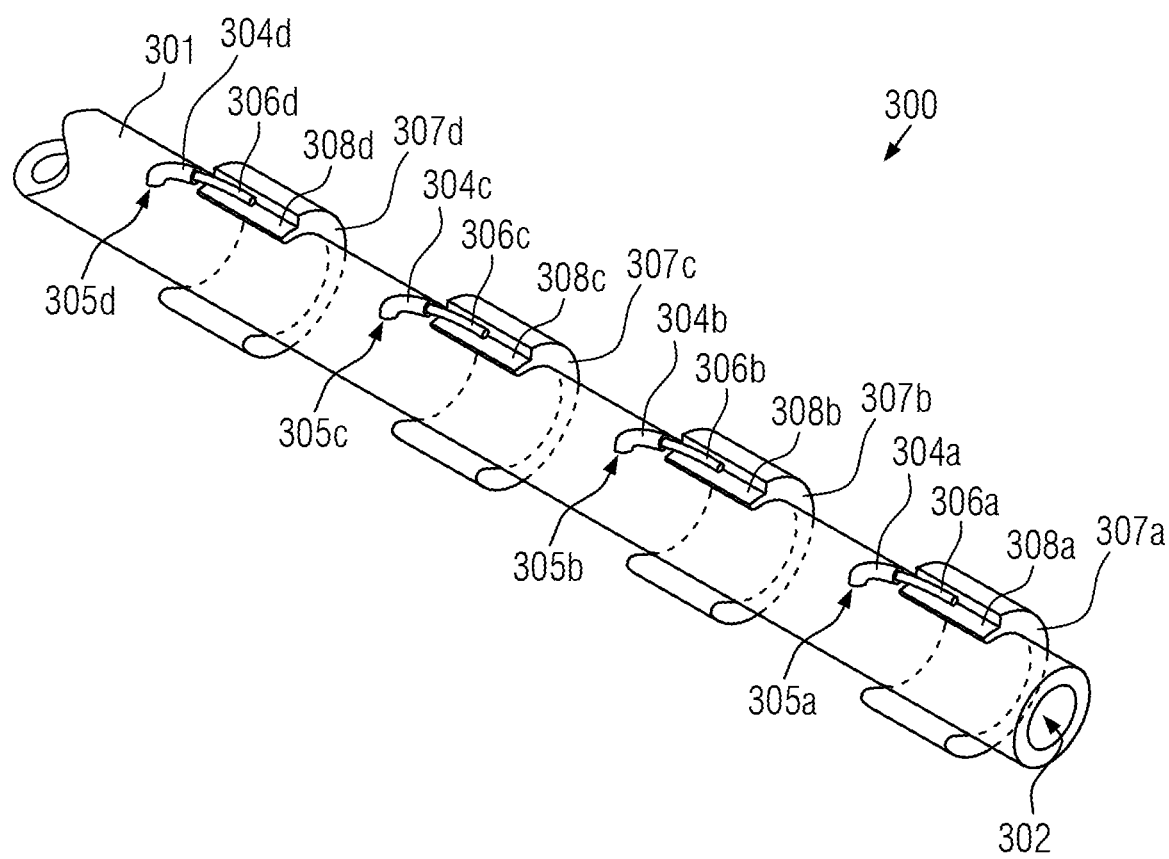
FIG. 8 schematically illustrates the proximal end of another lead body usable with embodiments of an electrical connector cap.

As can be taken from FIG. 8, in a further embodiment, an implantable lead member 300 usable with an electrical connector cap according to the previous aspects of the present disclosure can still comprise an elongated body 301, which is here also essentially tubular. However, unlike in the embodiments described with respect to FIGS. 5 to 7, the lead body 301 only has one lumen 302. Preferably, lumen 302 can be centered on the main axis of the lead body 301, but this aspect should not be considered as being limitative for the scope of the present disclosure. Thus, a lead body comprising a main lumen provided off-axis or comprising more than one lumen could also be used. Here also without limiting the scope of the present disclosure, the lead body 301 could be made by extruding or molding a biocompatible, preferably flexible, material such as polyurethane.

In a lead of the IS-4 type, up to four electrically conductive lines are typically needed and are usually all dedicated to low voltage. Thus, as shown in FIG. 8, four electrically conductive wires 304a, 304b, 304c, 304d can be arranged within lumen 302. In a preferred configuration (not visible), the electrically conductive wires 304a, 304b, 304c, 304d are arranged within lumen 302 in a spiral manner so as to leave a central portion of the lumen 302 free, for instance for the subsequent insertion of an optional contact pin assembly. In other embodiments, however, it would be possible to have electrically conductive wires 304a, 304b, 304c, 304d arranged in a simple straight configuration within lumen 302. The latter configuration is, however, not as advantageous as a spiral configuration, which offers better resistance to mechanical stress both in flexion and tension. Like in the embodiments described above, the number of electrically conductive lines and configuration of the wires should not be viewed as being limitative for the present disclosure. Thus, in other embodiments, more or less electrically conductive lines and associated wires may be used.

In comparison with the embodiments described with reference to FIGS. 5 to 7, FIG. 8 also illustrates another manner of realizing proximal electrically conductive members of a lead member usable in combination with an electrical connector cap according to the disclosure. As mentioned above in relation to the proximal electrically conductive members 78, 79, 80 of the embodiments illustrated in FIGS. 4A and 4B, proximal electrically conductive members can be achieved as emerging junctions and/or as ring-shaped elements. The latter configuration(s) will be described hereafter.

As shown in particular in FIG. 8, at least some of the electrically conductive wires 304a, 304b, 304c, 304d can be connected to ring-shaped proximal electrically conductive members 307a, 307b, 307c, 307d provided, in particular clipped and/or slid on the outer circumference of the lead body 301, towards the proximal end thereof. In view of using the lead member 300 in combination with an electrical connector cap according to other aspects of the disclosure, at least some of the ring-shaped proximal electrically conductive members 307a, 307b, 307c, 307d can be spaced apart from one another in an analog manner to the spacing between electrically conductive members of an electrical connector cap. For instance, at least the three ring-shaped proximal electrically conductive members 307a, 307b, 307c could be spaced apart in accordance with electrically conductive members 28, 29, 30 of electrical connector cap 20 of the embodiments illustrated in FIGS. 2A and 2B, as illustrated in particular in FIG. 9.

As also shown in FIG. 8, ring-shaped proximal electrically conductive members 307a, 307b, 307c, 307d do not need to be closed rings and can be provided as open rings. Preferably, the circumference of ring-shaped proximal electrically conductive members 307a, 307b, 307c, 307d can extend over at least about 180°, or even more. Rounded ends and at least 180° can facilitate the subsequent mounting of an electrical connector cap such as electrical connector cap 20 to form an implantable lead assembly like lead assembly 310 illustrated in FIGS. 9 and 10. Furthermore, an outer diameter of ring-shaped proximal electrically conductive members 307a, 307b, 307c, 307d can correspond to the diameter of the lumen in an electrical connector cap according to the disclosure. In the illustrated embodiments, as shown in FIGS. 9 and 10, an outer diameter of ring-shaped proximal electrically conductive members 307a, 307b, 307c, 307d can correspond to the diameter of the lumen 22 within electrical connector cap 20. In addition, as can be taken from FIG. 8, in order to better secure them to the lead body 301, the internal diameter of ring-shaped proximal electrically conductive members 307a, 307b, 307c, 307d can correspond essentially to an outer diameter of the lead body 301. Furthermore, the open ring-shaped proximal electrically conductive members 307a, 307b, 307c, 307d could be pressed as desired in order to be better attached, in particular clipped, on the lead body 301.

The electrical connection between electrically conductive wires 304a, 304b, 304c, 304d and ring-shaped proximal electrically conductive members 307a, 307b, 307c, 307d can be achieved in various ways. In the embodiments illustrated in particular in FIG. 8, electrically conductive wires 304a, 304b, 304c, 304d can exit lumen 302 via respective through holes 305a, 305b, 305c, 305d such that respective non-insulated end portions 306a, 306b, 306c, 306d of each wire 304a, 304b, 304c, 304d are exposed out of the lead body 301. In a somewhat similar manner to the embodiments referring to FIGS. 5 to 7, the exposed end portions 306a, 306b, 306c, 306d of each wires 304a, 304b, 304c, 304d could, in principle, form a sort of emerging electrical junctions. Thus, in principle, they could be used as proximal electrically conductive members on their own. However, compared to the emerging junctions realized by electrical contact 206a in the embodiments illustrated in FIGS. 5 to 7, the exposed end portions 306a, 306b, 306c, 306d would be less reliable. Thus, using ring-shaped proximal electrically conductive members 307a, 307b, 307c, 307d is preferred in this configuration.

Alternatively, instead of respective through holes 305a, 305b, 305c, 305d, it could be possible to provide a slit along the proximal end of the lead body 301, such that the exposed end portions 306a, 306b, 306c, 306d would protrude out of the lead body 301 via said slit. In this alternative configuration, after arranging the emerging end portions 306a, 306b, 306c, 306d, such a slit could then be closed or glued together, even roughly, using for instance a polymer adhesive.

Furthermore, at least through holes 305a, 305b, 305c can preferably be spaced apart in accordance with electrically conductive members of an electrical connector cap according to the disclosure. Here, like ring-shaped electrically conductive members 307a, 307b, 307c, at least through holes 305a, 305b, 305c, and hence at least the exposed end portions 306a, 306b, 306c, can also be spaced apart in accordance with electrically conductive members 28, 29, 30 of electrical connector cap 20 of the embodiments illustrated in FIGS. 2A and 2B.

In any case, when the ring-shaped proximal electrically conductive members 307a, 307b, 307c, 307d are mounted on the lead body 301, the exposed end portions 306a, 306b, 306c, 306d of electrically conductive wires 304a, 304b, 304c, 304d can be brought in contact with a respective one of the ring-shaped proximal electrically conductive members 307a, 307b, 307c, 307d. The exposed end portions 306a, 306b, 306c, 306d could then be fixedly secured to the ring-shaped proximal electrically conductive members 307a, 307b, 307c, 307d, for instance by laser welding or any other equivalent technology. In order to protect the underlying lead body 301 from being damaged during such a process, the ring-shaped proximal electrically conductive members 307a, 307b, 307c, 307d can be provided with an optional groove or notch for accommodating the exposed end portions 306a, 306b, 306c, 306d of electrically conductive wires 304a, 304b, 304c, 304d. Here, FIG. 8 shows that each ring-shaped proximal electrically conductive members 307a, 307b, 307c, 307d is provided with a respective notch 308a, 308b, 308c, 308d receiving a respective exposed end portion 306a, 306b, 306c, 306d. As mentioned above, laser welding or equivalent technologies can be used to fixedly secure end portion 306a, 306b, 306c, 306d to members 307a, 307b, 307c, 307d, in particular to notches 308a, 308b, 308c, 308d.

Figure 9:
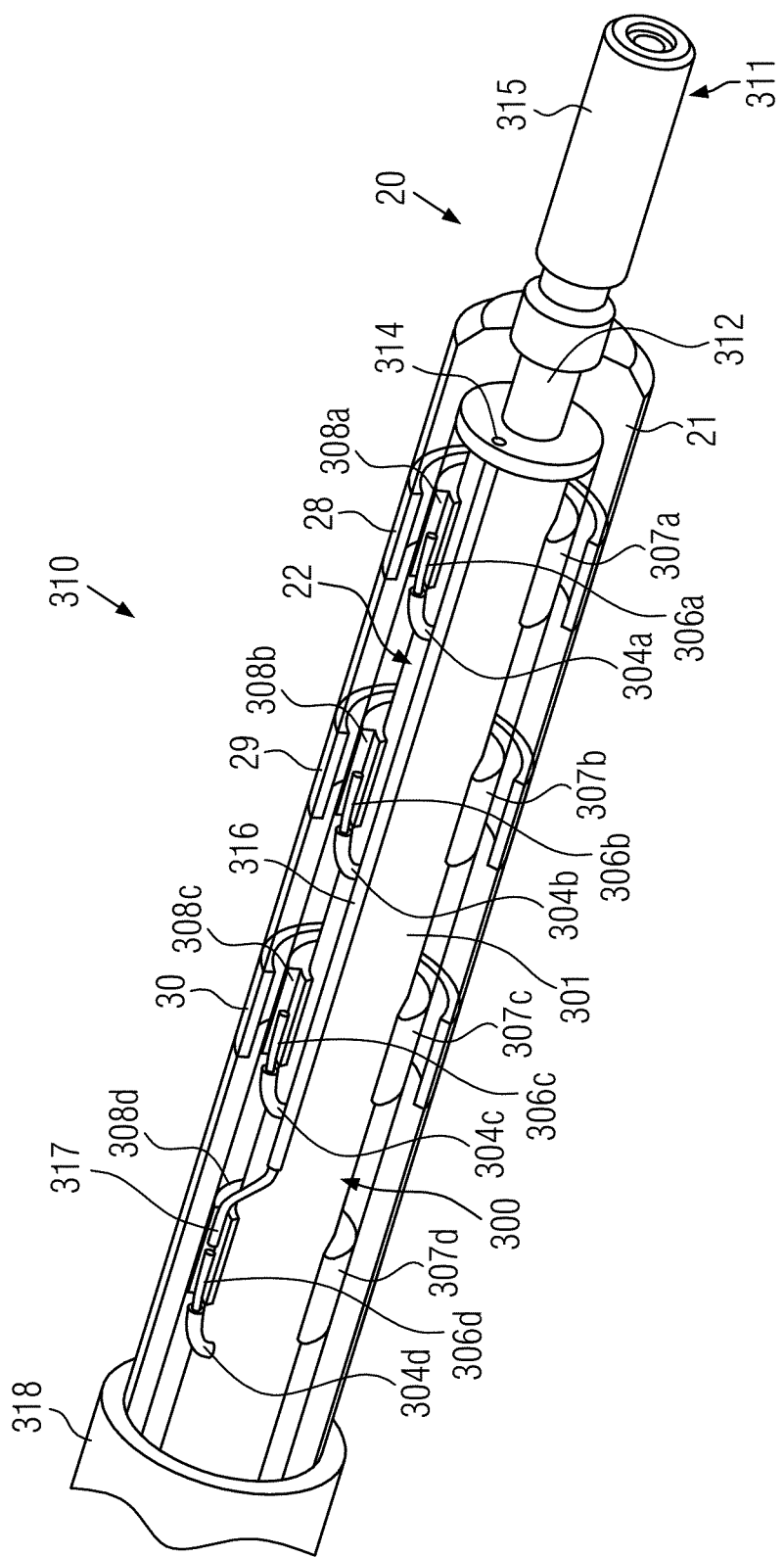
FIG. 9 schematically illustrates a longitudinal partially sectional view of embodiments of an implantable lead assembly, comprising the electrical connector cap of the embodiments illustrated in FIGS. 2A and 2B mounted over the proximal end of a lead body according to the embodiments illustrated in FIG. 9.
Figure 10:
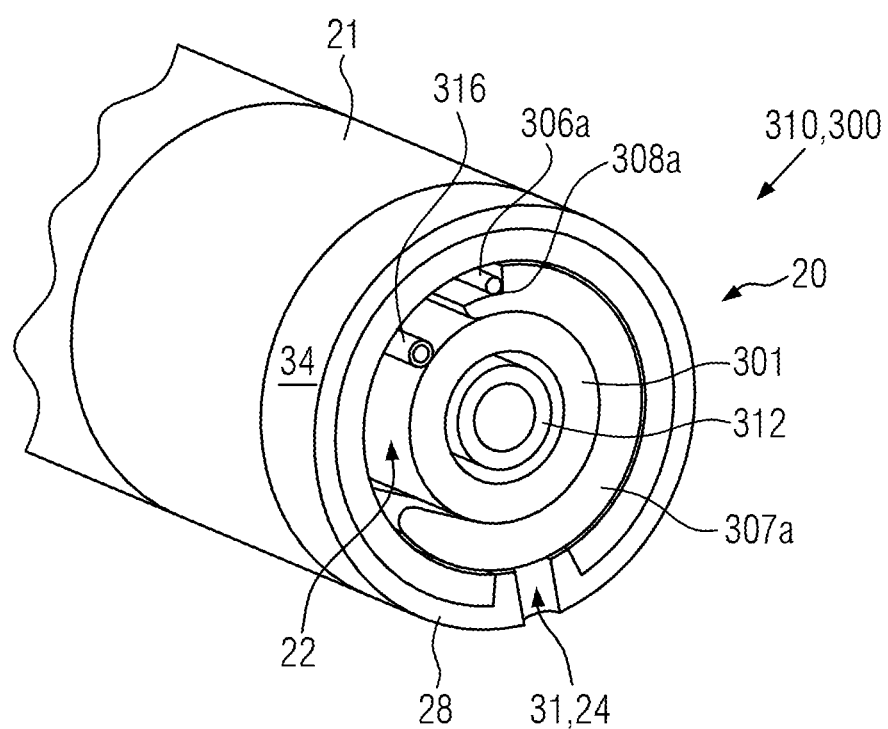
FIG. 10 schematically illustrates a cross-sectional view of the implantable lead assembly illustrated in FIG. 9 detailing a contact area between respective electrically conductive members of the lead and of the electrical connector cap.

However, the connection between the emerging exposed end portions 306a, 306b, 306c, 306d and the ring-shaped proximal electrically conductive members 307a, 307b, 307c, 307d does not need to be limited to the embodiments illustrated in FIGS. 8 to 10. In other embodiments, proximal electrically conductive members of a lead member of the present disclosure could be realized in a similar manner to the electrically conductive members 28, 29, 30 or 50 described above. Accordingly, the ring-shaped electrically conductive members 307a, 307b, 307c, 307d could be provided with an inner protrusion extending in through holes 305a, 305b, 305c, 305d in order to establish the electrical connection when the end portions 306a, 306b, 306c, 306d of electrically conductive wires 304a, 304b, 304c, 304d do not emerge from the lumen 302.

In other words, the present disclosure allows providing proximal electrically conductive members of a lead member as emerging junctions, ring-shaped elements, or a combination of both. As already mentioned with respect to previous embodiments, the number of proximal electrically conductive members in a lead member according to the disclosure is not limited to the configurations of the illustrated embodiments and should be adapted to the number of electrically conductive lines required by the application (lead with a standard or a non-standard connector member; cardiac/pulmonary/nervous system/brain applications, etc.).

Next, FIG. 9 illustrates a longitudinal partially sectional view of an implantable lead assembly 310 formed by the implantable lead member 300 illustrated in FIG. 8 onto which an electrical connector cap according to other aspects of the disclosure has been mounted. Here, for the sake of simplicity, the electrical connector cap 20 (or 60) of the embodiments illustrated in FIGS. 2A and 2B (or 4A and 4B) is shown. In turn, FIG. 10 illustrates a cross-sectional view of the implantable lead assembly 310. The lead assembly 310 is substantially similar to the lead assemblies 100, 210 of the previous embodiments, except that this example is intended to illustrate a pacing/stimulating lead of the IS-4 type. The reader is, therefore, referred also to the disclosure above for further details.

Optionally, before mounting the electrical connector cap 20 on the proximal end of the lead member 300, a contact pin assembly 311 can have been mounted in the lumen 302 of the lead body 301. As can be taken from FIG. 9, the contact pin assembly 311 can comprise an axial contact pin 312, partly accommodated in the main lumen 302 of lead body 301, and partly protruding from the proximal end of the lead body 301. Thus, the axial contact pin 312 can also protrude out of the proximal end of the mounted electrical connector cap 20 in lead assembly 310.

If so desired, the contact pin assembly 311 can comprise further elements such as a one or more optional stop and/or seal rings, here for instance ring 314 which abuts against the free end of the lead body 301 and could be provided integrally with axial contact pin 312. Since the illustrated embodiments represent a lead assembly 310 using the IS-4 standard, axial contact pin 312 is connected to one of the various electrically conductive lines. In this respect, because of the chosen standard and corresponding necessary pre-defined spacing between the electrically conductive members 28, 29, 30 of the electrical connector cap 20, it is necessary to define a corresponding spacing between corresponding ring-shaped proximal electrically conductive members 307a, 307b, 307c, 307d. Thus, the three most proximal ring-shaped electrically conductive members 307a, 307b, 307c can be provided, in particular arranged, in order to meet the standard spacing of the electrically conductive members 28, 29, 30 of the electrical connector cap 20. Accordingly, the fourth ring-shaped proximal electrically conductive member 307d, which is attached to fourth wire 304d, is free to be connected to the axial contact pin 312, for instance to the ring 314. As shown in FIG. 9, in these embodiments, this is achieved by means of an electrically conductive wire 316 which is connected, at one end, to the axial contact pin 312, and at the other end 317, to the fourth ring-shaped proximal electrically conductive member 307d. The latter connection can be achieved in similar manner to what was described above with respect to the exposed end portions 306a, 306b, 306c, 306d of electrically conductive wires 304a, 304b, 304c, 304d.

In alternative embodiments, the connection of an electrical line to the axial contact pin 312 could be provided in a different manner. For instance, the fourth ring-shaped proximal electrically conductive member 307d and the additional electrically conductive wire 316 could be avoided, whereby the exposed end portion 306d would not need to emerge from the lead body 301 and could be connected directly to the axial contact pin 312, the electrically conductive wire 304d being then provided with the necessary length. However, in the illustrated embodiments, the fourth low voltage electrical line is provided in an analog manner to the other three lines, namely using a corresponding ring-shaped electrically conductive member 307a, 307b, 307c, 307d in order to standardize and/or streamline the manufacturing and/or assembly process(es).

Since the embodiments illustrated in FIGS. 9 and 10 represent a lead assembly 310 using the IS-4 standard, in analog manner to what was described above for the previous embodiments, the part of the axial contact pin 312 of the contact pin assembly 311 protruding through the proximal end of the body 21 of the electrical connector cap 20 can be configured according to the desired connectivity standard. To this purpose, a terminal end 315 configured, in particular shaped, for the desired specific standard, here the IS-4 standard, can be provided over the protruding part of the axial contact pin 312, as illustrated in particular in FIG. 9. Like in the previous embodiments, it is understood that this optional terminal end 315 could be attached using known technologies, in particular welding, laser welding, or the like. Again, the particular configuration of the optional terminal end 315 should not be viewed as a limiting factor for the present disclosure.

When the electrical connector cap 20 is mounted over the proximal end portion of the lead member 300, as shown in FIGS. 9 and 10, because its electrically conductive members 28, 29, 30 extend into lumen 22 via respective through holes 24, 25, 26 of the elongated body 21 of the electrical connector cap 20, it is possible to arrange the part of an electrically conductive member 28, 29, 30 extending in a respective through hole 24, 25, 26 of the electrical connector cap 20 so as to face a respective one of the most proximal ring-shaped electrically conductive members 307a, 307b, 307c. In the embodiments illustrated in FIGS. 9 and 10, the electrically conductive members 28, 29, 30 are realized like the preferred variant of ring-shaped electrically conductive member 50 of the embodiments illustrated in FIG. 3. Thus, when the electrical connector cap 20 is mounted on the proximal end of the lead member 300, the respective inner protrusion of an electrically conductive member 28, 29, 30 can consequently even establish a physical contact with an underlying respective electrical contact or contact port of lead member 300. As can be taken from FIG. 10, in these embodiments, the inner protrusion of each electrically conductive member 28, 29, 30 faces and is in contact with an area of the outer surface of the corresponding one of the three most proximal ring-shaped electrically conductive members 307a, 307b, 307c. Although the view of FIG. 10 details the contact between electrically conductive member 28 and the proximal ring-shaped electrically conductive member 307a, the skilled person will appreciate that analog configurations can be reached between electrically conductive member 29 and proximal ring-shaped electrically conductive member 307b, as well as between electrically conductive member 30 and proximal ring-shaped electrically conductive member 307c.

Furthermore, as also mentioned with respect to some of the previous embodiments, the through hole 31, 32, 33 extending through the inner protrusion can facilitate visual control of the position of the underlying contact ports, here the three most proximal ring-shaped electrically conductive members 307a, 307b, 307c, relative to the electrically conductive members 28, 29, 30. It is, therefore, possible to control the mounted position of the electrical connector cap 20 on the proximal end of the lead body 301. The through hole 31, 32, 33 can also facilitate using techniques such as laser welding in order to fixedly secure one or more, preferably all, of the electrically conductive members 28, 29, 30 to the corresponding underlying ring-shaped electrically conductive members 307a, 307b, 307c.

Furthermore, as mentioned above, it is optionally also possible to further attach the electrical connector cap 20 to the lead member 300, in particular to the lead body 301, for instance by injecting an adhesive in the space between the lead body 301 and the electrical connector cap 20. This is also advantageous, as it provides additional insulation between the four electrical lines.

Thus, it is possible to achieve an implantable lead assembly 310 which can be used, in particular, for cardiac sensing and/or pacing when combined with a dedicated housing comprising corresponding IS-4 type sockets. However, as mentioned above, it is to be understood that the particular connectivity standard is not limitative for the scope of this disclosure. On the contrary, the present disclosure is intended to illustrate the flexibility of the disclosure, with which it is possible to provide implantable leads of various configurations. In the specific cases of IS-4 and DF-4 connections, the present disclosure is particularly advantageous, as it allows using the same electrical connector cap.

In any case, as illustrated in FIG. 9, in some embodiments, an implantable lead assembly 310 can comprise one or more protective and/or reinforcing and/or insulating sleeves like sleeve 318, which can be slid over the lead body 301 and, preferably, also over a rear or distal portion of the electrical connector cap 20 and be attached thereto, for instance using an adhesive and/or mechanical means. Here also, optional sleeve 318 could be used to prevent body fluids from penetrating, in particular filtering, into the distal portion of the electrical connector cap 20, thereby increasing the prevention against electrical shortages. To this purpose, the optional sleeve 216 could be made of silicon or any other suitable flexible biocompatible material.

Thus, with the present disclosure, it is possible to achieve implantable lead assemblies such as lead assemblies 100, 210, 310, in which any interconnection forming electrical lines between the distal and proximal ends of a lead member are moved inside the electrical connector cap. In doing so, in contrast with known implantable leads, the disclosure allows completely avoiding creating weakened areas at the level of the lead body emerging from the rear or distal end of a connector member. Indeed, with the present disclosure, any interconnections are now realized inside the electrical connector cap, between electrically conductive members (or contact ports) of the electrical connector cap and proximal electrically conductive members (or contact ports) of the proximal end portion of the lead member.

In particular, an advantage of the present disclosure is that a standardized electrical connector cap with a high added value can be produced in a single line of production while being compatible with more than one connectivity standard. For instance, the present disclosure provides a single standardized electrical connector that can be compatible, without modification, with both the IS-4 and the DF-4 standards.

Furthermore, an advantage of the present disclosure is that the construction of an implantable lead or lead assembly can be made more reliable than in the classic approach, as no electrical interconnection is necessary within the lead member, especially in the area immediately following the distal opening of the electrical connector cap, which is the area known to be subject to intensive mechanical stress. Indeed, with the present disclosure, the interconnections are realized in a reliable manner between the proximal end of the lead member and the electrical connector cap, in a protected environment, directly between each electrically conductive member of the electrical connector cap and a corresponding proximal electrically conductive member of the lead member.

Furthermore, embodiments of the present disclosure also allow, in addition to the improved mechanical stability, avoiding electrical shortages between electrically conductive lines, in particular between two high voltage lines.

The invention claimed is:

1. An electrical connector cap configured to be mounted over an end of an implantable lead, the electrical connector cap comprising:
   an elongated body having at least one lumen configured to be mounted over the end of the implantable lead and at least one through hole extending from an outer surface of the elongated body into the at least one lumen; and
   at least one electrically conductive member extending completely around an outer circumference of the elongated body over said at least one through hole of the elongated body;
   wherein said at least one electrically conductive member comprises at least one through hole aligned with the at least one through hole of the elongated body to form an opening extending from an outer surface of the at least one electrically conductive member into the lumen; and
   wherein the at least one electrically conductive member is configured to at least partially contact a corresponding electrically conductive member positioned on an outer circumference of the end of the implantable lead.

2. The electrical connector cap according to claim 1, wherein the at least one through hole comprises two or more through holes and wherein the two or more through holes are offset longitudinally along the elongated body and/or offset are in a circumferential direction of the elongated body with respect to each other.

3. The electrical connector cap according to claim 1, wherein the elongated body is a one-piece component made of a biocompatible insulating material.

4. The electrical connector cap according to claim 1, wherein the diameter of the lumen is constant over a main central portion of the elongated body and decreases stepwise at a proximal end portion of the elongated body.

5. The electrical connector cap according to claim 1, wherein the diameter of the lumen is larger at a distal end portion of the elongated body than at a main central portion of the elongated body.

6. The electrical connector cap according to claim 1, wherein a distal end portion of the elongated body comprises at least one additional through hole, the at least one additional through hole free of any electrically conductive member.

7. The electrical connector cap according to claim 1, wherein an outer diameter of the elongated body decreases in a stepwise manner at a distal end portion thereof.

8. The electrical connector cap according to claim 1, wherein the elongated body further comprises at least one recessed area along the outer circumference, said at least one through hole of the elongated body positioned in the at least one recessed area, and said at least one electrically conductive member being arranged in the corresponding at least one recessed area.

9. The electrical connector cap according to claim 8, wherein said at least one recessed area extends along a complete outer circumference of the elongated body and said at least one recessed area is essentially annular.

10. The electrical connector cap according to claim 1 wherein an outer surface of said at least one electrically conductive member is flush with the outer surface of the elongated body.

11. The electrical connector cap according to claim 1, wherein said at least one electrically conductive member has an inner protrusion extending in the respective through hole of the elongated body extending radially inwards.

12. The electrical connector cap according to claim 11, wherein said inner protrusion is flush with the inner surface or lumen of the elongated body.

13. The electrical connector cap according to claim 11, wherein said at least one through hole of said at least one electrically conductive member extends through said inner protrusion radially.

14. An implantable lead assembly comprising:
   an elongated lead body having a proximal end being the end of the elongated lead body configured to be connected to a housing of an active implantable medical device, a distal end being the opposite end of the elongated lead body configured for sensing and/or stimulating a tissue, a first electrically conductive member positioned on an outer circumference of the elongated lead body, and at least one lumen; and
   at least one electrically conductive wire arranged in said at least one lumen, said at least one electrically conductive wire being in electrical contact with the first electrically conductive member;
   wherein the implantable lead assembly further comprises, mounted over the proximal end, an electrical connector cap including a second electrically conductive member, the electrical connector cap arranged such that the first electrically conductive member at least partially contacts the second electrically conductive member,
   wherein the electrical connector cap comprises an elongated body having at least one through hole extending from an outer surface of the elongated body of the electrical connector cap into the at least one lumen,
   wherein the second electrically conductive member is arranged on an outer circumference of the elongated body of the electrical connector cap over said at least one through hole of the elongated body of the electrical connector cap, and
   wherein the second electrically conductive member comprises at least one through hole aligned with the at least one through hole of the electrical connector cap to form an opening extending from an outer surface of the second electrically conductive member into the lumen.

15. The implantable lead assembly according to claim 14, wherein the first electrically conductive member is an emerging electrical junction and/or an at least partially ring-shaped element.

16. The implantable lead assembly of claim 14, wherein the first electrically conductive member is at least partially ring-shaped, and wherein an outer diameter of the first electrically conductive member corresponds substantially to an inner diameter of a lumen of the electrical connector cap.

* * * * *